United States Patent
Zhou

(10) Patent No.: US 9,045,409 B2
(45) Date of Patent: Jun. 2, 2015

(54) PROCESS FOR PRODUCING PURIFIED TEREPHTHALIC ACID

(71) Applicant: Xiangjin Zhou, Beijing (CN)

(72) Inventor: Xiangjin Zhou, Beijing (CN)

(73) Assignee: Xiangjin Zhou, Beijing (CN)

( * ) Notice: Subject to any disclaimer, the term of this patent is extended or adjusted under 35 U.S.C. 154(b) by 81 days.

(21) Appl. No.: 13/925,225

(22) Filed: Jun. 24, 2013

(65) Prior Publication Data

US 2013/0281731 A1    Oct. 24, 2013

Related U.S. Application Data

(63) Continuation-in-part of application No. 12/736,130, filed on Oct. 25, 2010, now abandoned.

(51) Int. Cl.
   *C07C 51/16* (2006.01)
   *C07C 51/255* (2006.01)
   *C07C 51/265* (2006.01)

(52) U.S. Cl.
   CPC ................................. *C07C 51/265* (2013.01)

(58) Field of Classification Search
   CPC ........ C07C 51/42; C07C 63/307; C07C 45/36
   See application file for complete search history.

(56) References Cited

U.S. PATENT DOCUMENTS

| | | | |
|---|---|---|---|
| 2001/0041811 A1* | 11/2001 | Sikkenga et al. | 562/416 |
| 2007/0155985 A1* | 7/2007 | Wonders et al. | 562/410 |
| 2009/0062563 A1* | 3/2009 | Sijben et al. | 562/416 |

OTHER PUBLICATIONS

English Translation of PCT Search Report ISR, Sep. 2009.*
English Translation of the PCT Written Opinion of the International Search Authority, Sep. 2010.*

* cited by examiner

*Primary Examiner* — Sudhakar Katakam
*Assistant Examiner* — Jennifer C Sawyer
(74) *Attorney, Agent, or Firm* — CBM Patent Consulting, LLC

(57) ABSTRACT

A new process for the production of purified terephthalic acid (PTA) is disclosed to keep terephthalic acid (TA) in dissolved state during the process of oxidation reaction, to obtain intermediate product crude terephthalic acid (CTA) not containing the two impurities of 4-carboxyl benzaldehyde (4-CBA) and p-methyl benzoic acid (PT acid), so that it can eliminate the "purified" production process, and reduce the consumptions of raw materials, acetic acid, fuel and power, and water, thereby saving production costs.

3 Claims, 4 Drawing Sheets

PROCESS FOR PRODUCING PURIFIED TEREPHTHALIC ACID

CROSS-REFERENCE TO RELATED APPLICATIONS

This application claims the benefits of U.S. application Ser. No. 12/736,130, filed on Oct. 25, 2010, which is a continuation of International Application No. PCT/CN2009/000264, with an international filing date of Mar. 12, 2009, which is based on Chinese Patent Application No. 200810085014.2, filed Mar. 13, 2008. The entire disclosure of the above application is incorporated herein by references.

TECHNICAL FIELD

This invention applies to petrochemical industry field, which is a new process for producing petrochemical products.

BACKGROUND ART

Purified terephthalic acid (English ab. PTA) product is the raw material of polyethylene glycol terephthalate (polyester for short, English ab. PET).

Prepare the purified terephthalic acid (PTA) with paraxylene (PX) as raw material, compressed air or other oxygen-containing gases (oxygen for instance) as auxiliary material, acetic acid as solvent, cobalt acetate and manganese acetate as catalysts, and hydrobromic acid as cocatalyst, carry out the oxidation reaction at the relatively gentle temperature to obtain terephthalic acid (TA). The ion contents of cobalt, manganese and bromine—effective ingredients—in catalyst and cocatalyst generally range from 900 ppm to 2000 ppm, the ratio between cobalt, manganese and bromine is a little higher, generally in 1:1:1 or 1:2:3 or 1:2:2 and so on.

After the processes of oxidation reaction, terephthalic acid (TA) crystallization, separation, desiccation, etc., obtain the crude terephthalic acid (CTA, or TA), then dissolve the CTA in hot water, and send it to hydrogenation reactor at both high temperature and high pressure, carry out the hydrogenation reaction in the presence of Pd/C catalyst, reduce the 4-CBA into P-methyl benzoic acid (PT acid), the water solubility of PT acid is significantly higher than TA, so the TA and PT acid can be basically separated by the re-crystallizing of TA in aqueous solution. Then the purified terephthalic acid (PTA) is obtained by the water washing, centrifugal separating, filtering and drying of the TA. The PT acid and a little of TA in aqueous solution are returned to the oxidation reactor after which are concentrated and dehydrated.

The known research indicated that the oxidation reaction from paraxylene (PX) to terephthalic acid (TA) was a tandem reaction, it mainly underwent four reaction processes, firstly it was from PX to P-methyl benzaldehyde (TALD), secondly it was from TALD to PT acid, thirdly it was from PT acid to 4-CBA, fourthly it was from 4-CBA to TA. Four of the oxidation reactions were Irreversible reactions. Wherein the reaction velocity from PT acid to 4-CBA was the slowest under the same conditions, this reaction was the control step of the whole tandem reaction (see Reference: Weizheng Sun, et al, Kinetics of Liquid-Phase Catalytic Oxidation of p-Toluic Acid. *Chemical Reaction Engineering and Technology*. February, 2007. Issue 1, Vol. 23, p 8-12).

The design philosophy of this invention is as follows:

1. As to different reaction steps, offer the different reaction conditions, decrease the oxidation reaction temperatures from PX to p-methyl benzaldehyde (TALD) and from p-methyl benzaldehyde (TALD) to PT acid whose oxidation reaction conditions are not too rigorous, reduce the side reaction during which the solvent acetic acid is oxidized into carbon dioxide or carbon monoxide at high temperature as much as possible;

2. Increase the oxidation reaction temperature of control step of tandem oxidation reaction (from PT acid to 4-CBA), so as to increase the reaction velocity in this control step, then achieve the aim of increasing the whole oxidation reaction velocity;

3. Make sure that TA cannot form any crystal inside oxidation reaction, choose water as a secondary solvent during the oxidation processes from PT acid to 4-CBA and to TA, increase the temperature to enhance the TA solubility, but never enhance the acetic acid consumption.

According to this design philosophy, this invention innovated the designs for the new processes of reaction materials, separate the final oxidation product TA from PX and other intermediate products as much as possible, so that the main reaction materials can establish the upstream to downstream flow and processes from and to reactor. Instead of the current PX oxidation reactor inside, various materials, intermediate products and final product are mixed together, it should be a mixed oxidation reaction. This invention is a step oxidation reaction (or step-by-step reaction), this not only allows TA crystals to have no the impurities of 4-CBA and PT acid, but also allows the retention time of produced TA inside the oxidation reactor to shorten, thus reduting the raw materials consumption resulting from TA over-oxidizing and acetic acid consumption.

INVENTION CONTENT

This invention applies a new oxidation process for paraxylene (PX), which makes the major impurities of 4-carboxyl benzaldehyde (4-CBA) and p-methyl benzoic acid (PT acid) that can not be avoided in current production process are hardly contained in the intermediate product crude terephthalic acid (CTA) obtained from oxidation reaction, thereby, the "purified" production process for removing two of the impurities can be simplified or omitted, as a result, the consumptions of materials and fuel and power energy, acetic acid solvent, and water can be reduced, and the production costs can be saved. The quality of this product can exceed the current PTA product. Furthermore, the contents of 4-carboxyl benzaldehyde (4-CBA) and P-methyl benzoic acid (PT acid) contained in new terephthalic acid product can nearly be closed to zero, this product is called purified terephthalic acid, abbreviation is PPTA.

The perfect oxidation reaction design of this invention is that the oxidation reaction is carried out in the sequence of tandem oxidation reaction from PX to TA—step by step oxidation reaction or step oxidation reaction.

During the design of specific reaction processes, this invention designs the local and approximative plug-flow reaction processes. Inside the reactor, materials flow in a single direction from the inlet of reactants to the outlet of products (the conventional oxidation reactor was mixed inside, even equipped with a agitator). The oxidation reaction in plug-flow process stage is carried out in the successively sequence of tandem reaction from PX to TA, that is, the raw material PX newly added to reactor can not enter the later stage of the tandem reaction. Consequently, the target product TA obtained from oxidation reaction can be effectively separated from reactant PX and intermediates of oxidation reaction. FIG. 1 is the schematic diagram showing the oxidation reactor and the oxidation reaction process. Inside the reactor, reactants flow in single direction from the inlet of raw materials to the outlet of resultants. Unlike the past, inside the reactor, reactants are disorderedly a mixture. At the inlet of materials inside reactor, the molar ratio of reactant PX is 100%, the ratio of other resultants is 0%. With the position moving to the outlet, the PX molar ratio of the materials gradually decreases, while the molar ratio of intermediates from the reaction gradually increases, and also, the molar ratios of TALD, p-TA and 4-CBA are the maximum values (peak concentrations). At the outlet of reactants inside the reactor, the molar ratio of the reactant PX is 0%, the ratio of intermediates from the reaction is 0%; the molar ratio of the end product TA is 100%. At and near the outlet of resultants, control the reaction temperature in a zone so as to keep the temperature in such a zone above 288° C.; this zone is the so-called equilibrium zone. TA will be in a completely dissolved state at such a temperature, no TA crystals exist. 4-CBA leaves unprotected by crystals, so, all of 4-CBA molecules will be oxidized into TA molecules. Therefore, TA does not need to be refined. From the inlet of reactants to the outlet of resultants (as shown in FIG. 1), the temperature inside reactor ranges from 130° C. to 180° C., and then, underwent the transition to 210° C., 260° C. and 288° C., respectively. From the inlet of reactants to the outlet of resultants, when adding the solvent from the outside to the inside of the reactor, the moistures in acetic acid are 6%, 10%, 20% and 80%, respectively. The moisture level in the solvent is high where the internal temperature in reactor is high.

Due to the difference from mixed oxidation, the material flows inside reactor has the upstream and downstream relationship, the outlet area of target oxidation product TA can be effectively separated from the inlet area of raw materials, this kind of separation is not completely closed in space, but the materials at two of the areas can not directly be mixed with each other because of the presence of materials flowing during the reaction.

REACTOR AND ITS STRUCTURE

Figure 1:
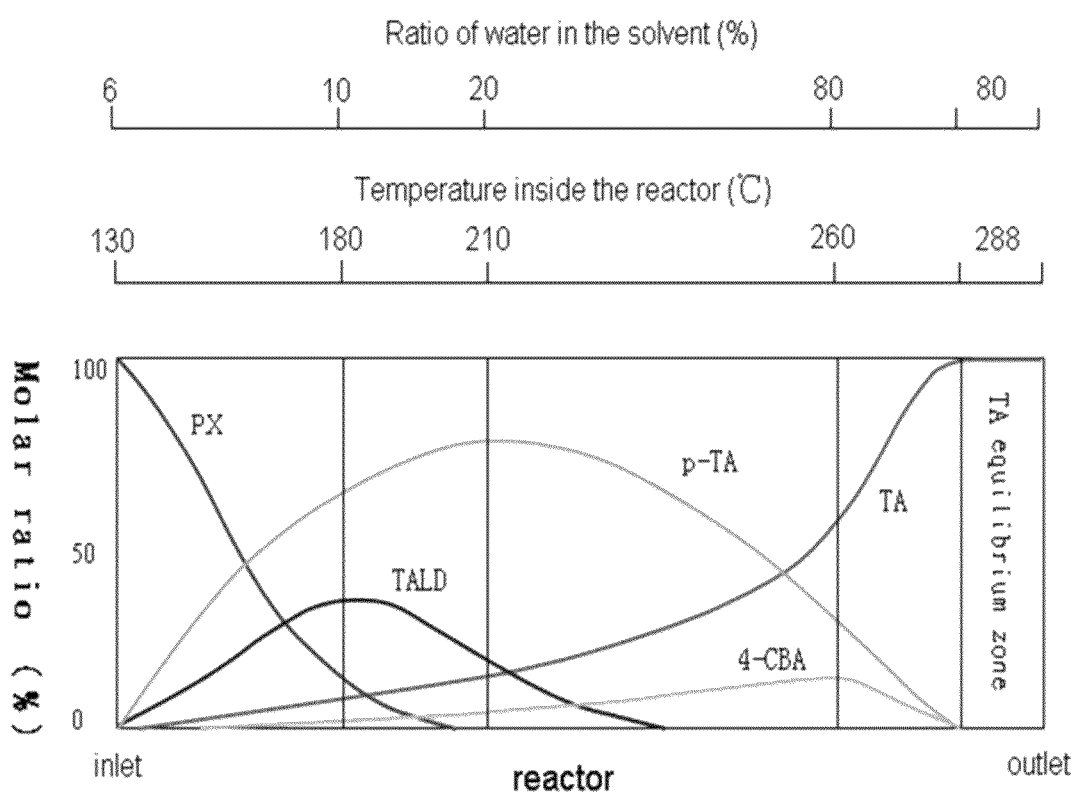
FIG. 1 The principle diagram of the reactor and reaction process.
Figure 2:
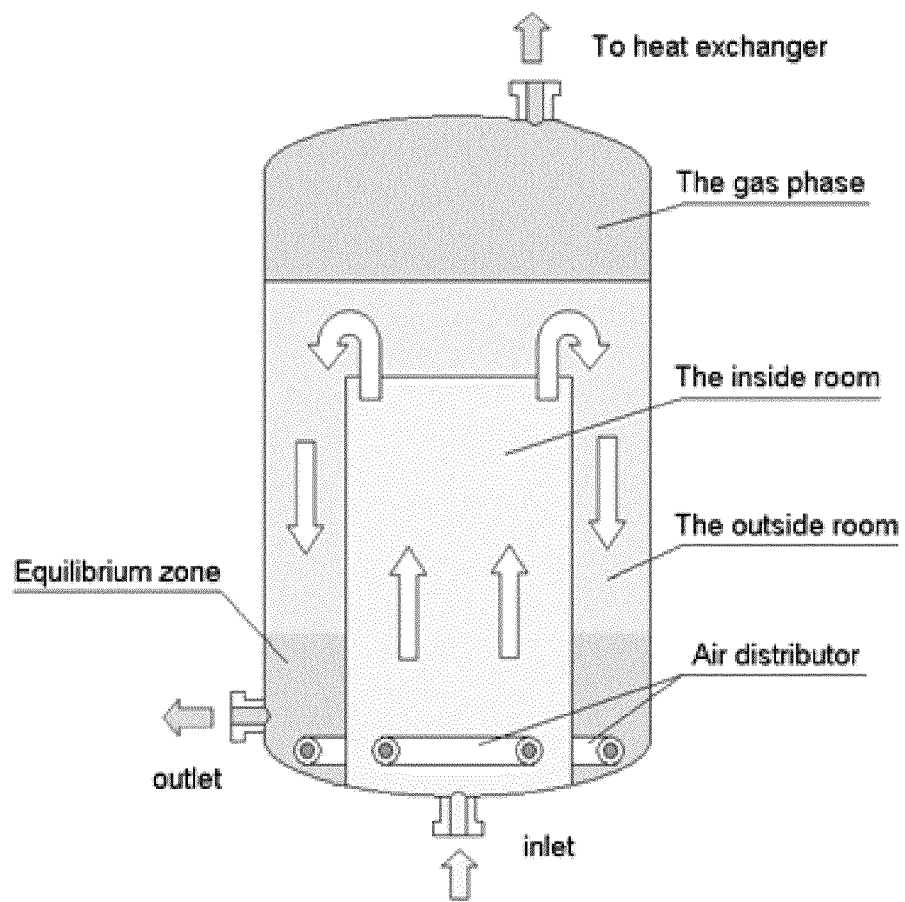
FIG. 2 The oxidation reactor with chamber and the outer chamber.

This invention has designed the oxidation reactor with the structure of inner and outer chambers (as shown in FIG. 2); the oxidation reactor with the structure of inner, medium, and outer chambers; horizontal plug-flow oxidation reactor; tower type plunger-flow oxidation reactor; and the tandem oxidation reactor combination of multiple reactors. Inside these reactors or their combination, the materials are similar to those in the plunger-flow or plug-flow process, the oxidation reactor is basically carried out in the sequence of tandem oxidation reaction.

The function of these reactors or their combination is to allow the materials earlier entered into reactor to carry out the oxidation reaction earlier, and the materials latter entered into reactor to carry out the oxidation reaction latter, the PX material and the final oxidation product TA staying at two ends of liquid phase materials flowing inside the reactor can not be mixed, so that a TA solution buffer area where the residual p-TA and 4-CBA can be oxidized into TA can exist at the end of liquid phase material flowing inside the reactor, and make sure that the materials come out from the oxidation reactor outlet (or from the end oxidation reactor outlet of oxidation reactor combination) and the PX, TLAD, p-TA, and 4-CBA etc. materials and intermediates are not contained in oxidation reaction materials entering into crystallizer, and the organic material phase of reactant only has TA. The organic material phase from PX to TA liquid phase materials (including PX, TALD, p-TA, 4-CBA, TA, etc.) for oxidation reaction materials establishes a material flow relationship between upstream and downstream processes, which is different to existing PX oxidation processes.

The existing PX oxidation process applies a mixed oxidation process, the liquid phase materials inside reactor—various materials, production and oxidized intermediates are mixed together.

Quantities of Compressed Air or Other Oxygen-Containing Gases:

Compressed air or oxygen as an auxiliary material, oxidation reactor with the structure of inner and outer chambers for instance, PX is fed thereto from the inner chamber of the oxidation reactor, in the outer chamber of the oxidation reactor, the compressed air or other oxygen-containing gas is excessively supplied, the concentration of liquid phase oxygen is higher, and PX do not participate in the reaction to contest the oxygen, the oxygen concentration using for PT acid oxidation is high, so the reaction velocity of control step of tandem oxidation reaction—from PT acid to 4-CBA is higher, therefore, the reaction of the whole tandem oxidation reaction is accelerated and the total consumption of acetic acid solvent is reduced. The throughput per volume increases. The reaction temperature from PT acid to 4-CBA can be increased, so the whole oxidation reaction velocity is increased.

Compressed air or other oxygen-containing gas enters the reactor from the inner chamber in multiple streams, and the air or oxygen-containing gas is sent to the outer chamber from bottom via a circle distributor. Alternatively, send the compressed air or other oxygen-containing gas into inner and outer chambers, respectively, via a circle distributor. The total flow rate of air or oxygen-containing gas shall be set according to the PX flow rate and oxygen concentration in reactor tail gas, so as to ensure that the oxygen concentration in tail gas emitted from tail gas condenser of reactor is less than 2-4%.

The precondition for directly using oxygen as auxiliary material is that the water proportion to solution in the oxygen added area is more than 40%, and under this condition, the oxidation reaction velocity may be very high, but the phenomena of violent oxidation reaction and reaction out of control do not occur.

Control the flow rates of the PX, compressed air or other oxygen-containing gas entering oxidation reaction to ensure that the TA solution discharged from reactor has no 4-carboxyl benzaldehyde (4-CBA) and P-methyl benzoic acid (PT acid). The 4-carboxyl benzaldehyde (4-CBA) and p-methyl benzoic acid (PT acid) are oxidized into terephthalic acid (TA) step by step in the oxidation reactor.

Both Reaction Temperature and Pressure:

The oxidation reaction pressure of this invention is about 0.1-8.0 MPaG, and the reaction temperatures are between from about 90° C. to 210° C. and from 210° C. to 350° C. respectively by control in zones.

As a single oxidation reactor (tower type oxidation reactor for instance), the temperature range of low temperature stage (upper stage) is from 120° C. to 246° C., and the typical temperature of low temperature stage (upper stage) is 160° C.; both temperature and pressure ranges at high temperature stage (lower stage) are from 180° C. to 350° C. and from 1.3 to 8.5 MPaG, respectively, and the ranges of typical temperature and pressure of high temperature stage (lower stage) are 288V and 7.5 MPaG, respectively.

As a oxidation reactor combination, the temperature and pressure of low temperature reactor (first oxidation reactor) are 90V-210V and 0.1-1.8 MPaG, and the typical temperature of low temperature reactor is 130° C., the pressure depends on temperature, the pressure is the saturated vapor pressure of liquid phase materials at this temperature. The temperature and pressure of high temperature reactor are from 180° C. to 350° C. and from 1.3 to 8.5 MPaG, respectively, and the typical temperature and pressure of high temperature reactor are 288° C. and 7.5 MPaG, respectively.

Control the reactor pressure by controlling the gas throughput of compressed air or other oxygen-containing gas and the outlet control valve for non-condensable gas from condenser system of reactor tail gas. Oxidation reactor temperature is the main control parameter, the reactor pressure changes as the saturated vapor pressure corresponding to the temperature.

Catalysts and Cocatalyst

The catalysts of cobalt acetate and manganese acetate and the cocatalyst of hydrobromic acid can be combined in many proportions, such as 1:1:1, 1:2:3, or 1:2.5:1, etc. The typical proportion is 1:1:1. The proportion of single ion mass content of cobalt, manganese, bromine to total ion mass content of catalyst is 1:30. The concentration range of catalyst (total ion mass content) is 50-3000 ppm (catalysts/(organic material phase+solvent)), the typical concentration is 1050 ppm. The general method for feeding catalyst is that three of the catalysts and cocatalyst, raw material, and solvent (including the recovered catalyst and solvent) are mixed and added to oxidation reactor together.

As an optimized method, add the catalysts of cobalt acetate and manganese acetate into the oxidation reaction zone from PX to PT acid, then add the hydrobromic acid as cocatalyst when the second methyl starts to be oxidized.

Solvent and a Secondary Solvent

Start solvent is acetic acid, a secondary solvent is water. Along with the processes of tandem oxidation reaction, acetic acid proportion in mixed solvent consisting of acetic acid and water decreases step by step, has gradients, but water proportion increases step by step. In solvent, acetic acid proportion decreases from 100% to 0%. The water proportion increases from 0% to 100%. The typical solvent gradient is that acetic acid proportion decreases from 94% to 20% step by step, and water proportion increases from 6% to 80%.

Add a great deal of water to reactor as the solvent of terephthalic acid (TA), 4-carboxyl benzaldehyde (4-CBA) and p-methyl benzoic acid (PT acid), so that the target product terephthalic acid (TA) obtained from oxidation reaction can be dissolved sufficiently, and that the intermediate product 4-CBA can be dissolved sufficiently, and that can be further oxidized into terephthalic acid.

During the oxidation processes from PX to TALD and from TALD to PT acid, acetic acid is the major solvent, the content range of water as a secondary solvent between 3% and 20%, and the typical water content is 6%.

During the oxidation processes from PT acid to 4-CBA and from 4-CBA to TA, water instead of acetic acid is the major solvent, the proportion of water to acetic acid is from 100:0 to 20:80, the typical proportion is 80:20. under the typical condition of mixed solvent consisting of water and acetic acid, the liquid phase temperature of oxidation reactor can be increased to 288° C., at this time, 40-45% of TA can be dissolved in solution, if choosing 30% to be the typical concentration of TA, there is no TA crystal, and still the consumption of acetic acid is very low.

Technical Features of this Invention

1. Apply the oxidation reactor with the structure which can separate the raw material PX and target product TA from oxidation reaction, so that the liquid phase materials for oxidation reaction can establish a upstream and downstream relationship in the sequence of the tandem oxidation reaction. Control the conditions of oxidation reaction to meet the crystallizer system requirements, make sure that, the paraxylene (PX), P-methyl benzaldehyde (TALD), p-methyl benzoic acid (PT acid) and 4-carboxyl benzaldehyde (4-CBA) of these reaction materials at this area have been all oxidized into terephthalic acid (TA) when target product terephthalic acid (TA) of oxidation reaction is being crystallized into solid, so there are no two impurities of 4-carboxyl benzaldehyde (4-CBA) and P-methyl benzoic acid (PT acid) in the intermediate product crude terephthalic acid (CTA) obtained from crystallization Inside oxidation reactor, add water to liquid phase materials in the oxidation reaction zone from 4-CBA to TA as a secondary solvent of TA, properly increase the reaction temperature, enhance the TA solubility in mixed solvent consisting of water and acetic acid, so that the TA obtained from reaction can be completely dissolved in solvent.

Also, the temperature in the reaction zone from PT acid to 4-CBA can be properly increased, so as to increase the reaction velocity of control step of tandem oxidation reaction, the water as solvent can be added to oxidation reaction zone from PT acid to 4-CBA step by step, also can be added to the reaction zone before producing PT acid.

Although the local reaction temperature may be high, the water content will be high in this area, so violent oxidation reaction will not occur.

2. Respectively control the quantities of compressed air of different areas inside oxidation reactor, increase the supply quantity of compressed air per liquid phase capability in the oxidation reaction zone from PT acid to 4-CBA. Respectively control the quantity of compressed air or other oxygen-containing gas to keep the oxygen content in tail gas is less than 2-4%.

3. By the methods of controlling the feeding quantities of PX, solvents of acetic acid and water, the vaporizing capacities and the recovering quantities of solvents, control the reaction product terephthalic acid (TA) concentration in liquid phase at oxidation reactor, make sure that this concentration is closed to, but less than the saturated solubility of terephthalic acid in the oxidation reaction condition, so that the terephthalic acid (TA) can not be crystallized inside oxidation reactor.

4. As an oxidation reactor with the structure of inner and outer chambers, the bottom of outer chamber is effectively separated from outlet of material at internal chamber, the quantity of compressed air per liquid phase capability at outer chamber is larger than internal chamber.

5. As an oxidation reactor with the structure of internal, medium, and outer chambers, the liquid phase at top of outer chamber is effectively separated from the liquid phase at top of medium chamber, the bottom of medium chamber is effectively separated from the inlet of materials at internal chamber, and the outlet of liquid phase materials at top of outer chamber is effectively separated from the inlet of materials at internal chamber.

6. As a horizontal oxidation reactor with the plug-flow reaction processes, the liquid phase at the end of reaction can not be mixed at will with liquid phase at the material inlet, from inlet of raw material to outlet of reaction material inside reactor, the oxidation reaction is basically carried out in the sequence of tandem oxidation reaction.

7. The tower type oxidation reactor with the approximative plunger-flow reaction processes.

8. Oxidation reactor combination with two or three or more tandem reactors can keep the oxidation reaction materials in approximative plug-flow state;

Two normal oxidation reactors are hardly to keep the oxidation reaction materials in an approximative plug-flow state, but the combination of "oxidation reactor with the structure of inner and outer chambers", or "oxidation reactor with the structure of internal, medium, and outer chambers", or "horizontal oxidation reactor with the plug-flow reaction processes", or "tower type oxidation reactor with the approximative plunger-flow reaction processes" can commendably keep the oxidation reaction materials in approximative plug-flow state.

9. The solvent water added to liquid phase materials inside oxidation reactor can be heated by the method of tube heat exchange, add water into tubes, the tube outlet is the place to adding water to liquid phase at reactor as a secondary solvent, and the end surface of water inlet of tubes is closed, but add water from the side. The tubes are buried at the upstream of liquid phase material flow of reactants, the liquid phase materials of reactants are at outside, and fetch the heat from reaction heat of upstream materials.

As a substitute for water supply by tubes, drill holes on the reactor wall, and supply water (or mixed solvent of acetic acid with high water content) to liquid phase at reactor, increase the water proportion in solvent.

Control the reaction product terephthalic acid (TA) concentration in liquid phase at oxidation reactor, make sure that this concentration is closed to, but less than the saturated solubility of terephthalic acid (TA) in the oxidation reaction condition, so that the terephthalic acid (TA) can not be crystallized inside oxidation reactor. Increase the concentration of terephthalic acid (TA) as much as possible (precondition is that TA does not crystallized during this process), the aim is to decrease the retention time of solvent per product output, and decrease the loss of acetic acid solvent resulted from oxidation.

By comparison with the current PTA production technology, under the precondition of the same reactor capability, the reaction velocity of oxidation reactor applying this invention can be quickened, total retention time of materials are shortened, output is increased, and the consumptions of organic materials, solvent, and fuel and power are reduced.

Terephthalic acid (TA) obtained from oxidation reactor is only crystallized in crystallizer, and the solid of relatively purified terephthalic acid (TA) can be obtained in crystallizer.

There are no paraxylene (PX), P-methyl benzaldehyde (TALD), 4-carboxyl benzaldehyde (4-CBA), and P-methyl benzoic acid (PT acid) in the oxidation reaction materials entering into crystallizer, they are oxidized into terephthalic acid (TA) before they leaving oxidation reactor.

Inside reactor, part of the reaction heat is removed by flash vaporization of solvent and water, the condenser on top of reactor exchange and recycle heat. A great deal of reaction heat are removed by flash vaporization of solvent in crystallizer system, the solvent vaporized recovers heat by crystallizer.

In the crystallizer, solvent is continuously flash vaporized by decreasing pressure and temperature, the TA concentration is increased but the saturated solubility coefficient is decreased along with the decreasing temperature, and TA is continuously crystallized out from solution, crystal particles are slowly accreting. Equip with stirrer on the crystallizer to keep the dimensions of crystal particles in a relatively uniformity. There are no 4-carboxyl benzaldehyde (4-CBA), and P-methyl benzoic acid (PT acid) in the solution, so the TA crystal does not contain 4-carboxyl benzaldehyde (4-CBA), and P-methyl benzoic acid (PT acid).

by the methods of multi-level crystallization and decreasing temperature step by step, most of the TA solid is separated from solvent, catalyst, and other impurities, by the methods of centrifugal separation, filtration, and dryness, remove the residual solvent, then water washing it to remove the water soluble impurities, finally, by the methods of centrifugal separation, filtration, and dryness again, obtain PPTA product.

The purified terephthalic acid (PPTA) product is suitable as the materials for food packaging, beverage bottle, pharmaceutical packaging, and as the polymer material of medical equipments, due to the lowest formaldehyde group content and the less than 5-15 ppm of 4-CBA and PT acid contents, it has the advantages of a more secure without poison.

If relaxing the requirement for the product quality, that is, produce it according to the current product quality standards of PTA, the consumption index of PX in this invention will be further decreased.

Specific Implement Methods

1. The Structure and Combination of Oxidation Reactor Oxidation reactor with the structure of inner and outer chambers FIG. 2 shows an oxidation reactor with both inner and outer chambers. Obviously, inside such a reactor, raw materials at inlet and oxydates at outlet cannot be well mixed.

Apply a built-in cylinder with the same axis to oxidation reactor to separate the inner and outer chambers of reactor, and the bottom of cylinder is connected with the internal wall of the bottom of main body of oxidation reactor. The interstice between the cylinder outside and internal wall of oxidation reactor main body is outer chamber, but the cylinder inside is the inner chamber of reactor. The height of cylinder is lower than the design standard level of reactor, so as to keep the liquid phase materials at the inner and outer chambers connected at the top of the reactor during the normal production processes. The supply quantity of compressed air or other oxygen-containing gas at the inner and outer chambers can be designed to be the same, and also can be designed that the quantity of compressed air or other oxygen-containing gas per liquid phase capacity at outer chamber is larger than that at internal chamber.

Set up one or two circle distributors at the bottom of outer chamber of reactor to supply the required compressed air or other oxygen-containing gas to outer chamber. The capacity of outer chamber is ¼ to ½ of that of internal chamber.

Sep up stirrer in the inner chamber of reactor, but the stirring intensity is depressed a lot compared to that in the condition of TA crystal occurring inside reactor formerly, but now the aim is to disperse the materials of PX, acetic acid, and catalyst etc. from inlet into liquid phase materials inside reactor as soon as possible, and so that a little of TA crystal can not deposit, but enter the outer chamber from the upside of cylinder.

Use the distributor to supply water to reactor from the upside of outer chamber of reactor to ensure that the produced TA can be completely dissolved into the mixed solvent of water and acetic acid. The downside temperature of outer chamber is up to 246° C. to 288° C.

The conditions of material flow are: at internal chamber, compressed air or other oxygen-containing gas comes in from the bottom in multi-entry (four-entry for instance), the fresh materials come in from bottom of inner chamber and enter reactor, and after the mixed reaction, enter the outer chamber. The produced water and carbon dioxide disperse upwards. At outer chamber, the liquid materials move from top to bottom, and the compressed air or other oxygen-containing gas disperse from downwards to upwards, and the produced water and carbon dioxide disperse upwards. The reaction heat is removed by the flash vaporization of solvent which enters into condenser on the top of reactor. The condenser recycles the heat by heat exchange. The condenser can be combined with the structure of segregation tower to separate the acetic acid and water entering into condensation tower. Water and acetic acid are sent into tanks respectively. Part of water return into the outer chamber to increase the proportion of water in solvent phase. Part of condensation water and acetic acid are mixed and sent into inner chamber to decrease the temperature of internal chamber. The production TA dissolves into the mixed solvent consisting of water and acetic acid, discharge from the bottom of outer chamber, and sent into the crystallizer system.

As a substitute, there is no stirrer in the oxidation reactor.

As a substitute, the materials can come in from the bottom of outer chamber, but come out from the bottom of internal chamber.

The proportion of outer chamber space to inner chamber space can be 4:1, or 3:1, or 2:1; and also can be 1:4, or 1:3, or 1:2.

An oxidation reactor with the structure of internal, medium, and outer chambers

Apply two built-in cylinders with the same axis to oxidation reactor to separate the oxidation reactor into the three chambers of internal, medium, and external. The bottom of small cylinder is connected with the internal wall of bottom of main body of oxidation reactor, and upside of small cylinder is immerged below design level. The small cylinder separates the oxidation reactor into internal and medium chambers. The bottom of big cylinder is hung in the air, its upside height is higher than the design level, the inside and outside of big cylinder are respectively fixed in the side walls of small cylinder and main body of reactor, also they can be fixed on the bottom of main body of reactor by the method of point supports on the bottom. The big cylinder separates the oxidation reactor into medium and outer chambers. The gas phases in internal, medium and outer chambers are connected, where the liquid phase capacities are the same (calculate as the liquid phase capacity completely separated by extended faces of cylinder).

Set up there of circle distributors at the bottom of internal, medium and outer chambers for compressed air or other oxygen-containing gas, the place for compressed air or other oxygen-containing gas at external and medium chambers is slightly higher than the height of bottom of big cylinder. The flow rates of compressed air or other oxygen-containing gas at the three chambers are the same. The distributor at inner chamber blows downwards, but the distributors for compressed air or other oxygen-containing gas at medium and outer chambers blow upwards. The conditions of material flow are: after mixed, the PX, acetic acid, and catalyst etc. come in from the bottom of outer chamber at reactor, and come out from bottom of internal chamber. The gas phases at internal, medium and outer chambers are connected, the reaction heat is removed from reactor by the flash vaporization of solvent. The condenser on top of reactor can be combined with the structure of segregation tower to separate the acetic acid and water entering into condensation tower. Water and acetic acid are sent into tanks respectively. Part of water return into the upside of medium chamber to increase the proportion of water in solvent phase. Part of condensation water and acetic acid are mixed and sent into outer chamber to decrease the temperature of outer chamber.

Use the distributor to supply water to reactor from the upside and mid-side of inner chamber of reactor to ensure that the produced TA can be completely dissolved into the mixed solvent of water and acetic acid. The temperature of inner chamber is up to 246° C. to 350° C., and the typical temperature is 288° C.

A Horizontal Plug-Flow Oxidation Reactor

The materials come in from one end of reactor and come out from the other end, set up several row and straight tube distributors for compressed air or other oxygen-containing gas. This reactor is approximative to plug-flow reactor. Set up spiral sheet propeller shaft in the reactor to slowly propel the materials along with the flowing direction of liquid phase, the spiral sheet propeller shaft do not need to contact with reactor internal wall, the materials propelling is only token, the main aim is to separate the chambers by dynamic method inside reactor, and decrease the disorder fluidity of liquid phase materials to ensure that the material flowing direction of liquid phase materials is basically carried out in the sequence of tandem oxidation reaction from PX to TA.

The gas phases at the upside of reactor are connected, part of solvent and water are vaporized, water, carbon dioxide, and nitrogen etc. are volatilized, then all enter the gas condensation system, and the heat is recycled and removed from reactor. A great deal of reaction heat are removed by flash vaporization of solvent in crystallizer, and recycled by heat exchange or removed by flash vaporization of solvent and entering into condenser (exchanger) on the top of reactor.

Use the distributor to supply water to reactor from the midstream and downstream of material flow (gas phase) of reactor to ensure that the produced TA can be completely dissolved into the mixed solvent of water and acetic acid. The end temperature of reactor is up to 246° C. to 350° C., and the typical temperature is 288° C.

Tower Type Plunger-Flow Oxidation Reactor

Figure 4:
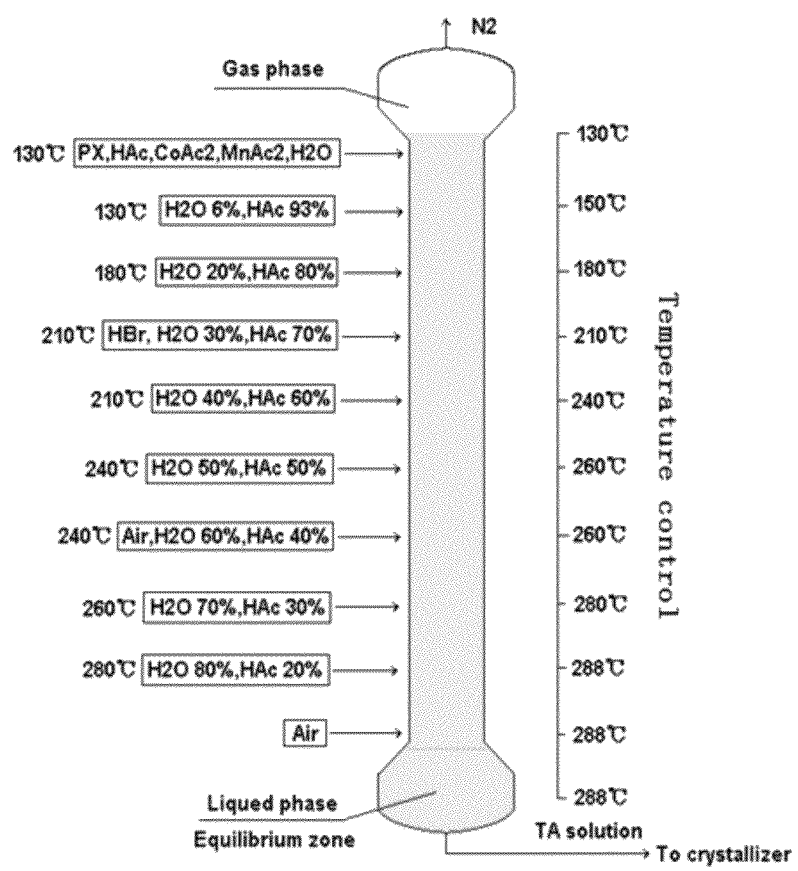
FIG. 4 Structure diagram of an upright oxidation reactor.

FIG. 4 shows the schematic diagram of the structure of a tower oxidation reactor. Its length-diameter ratio is very high; there is a large distance between the inlet of reactants and the outlet of resultants (increase the aspect ratio of reactor with the structure of inner and outer chambers or of reactor with internal, medium, and outer chambers, the reactor having the property of tower type oxidation reactor), inside set up the distributor for compressed air or other oxygen-containing gas in subsection, the carbon dioxide and nitrogen etc. inside reaction materials are removed by volatilization from the top of reactor, when it is used as a single oxidation reactor, avoid the solvent flash vaporization as much as possible, so as to ensure that the top of reactor is in low temperature oxidation area (exchange and fetch heat by water solvent tubes to keep the low temperature and decrease the consumption of acetic acid). The heat is removed by the flash vaporization of a great deal of solvent in crystallizer and the heat is recycled by heat exchange. Set up water inlet tubes inside reactor, fetch the heat from upstream materials, and use the heat to heat up the solvent water inside tubes as the solvent of downstream TA. Along with the adding of solvent water, the reaction temperature in the corresponding area is continuously increased to overcome the trend of reaction velocity deceasing resulted from the deceasing of reactant concentration, the temperature in high temperature stage is up to 246° C. to 350° C., and the typical temperature is 288° C.

Also, this is another way to exchange heat by tangling tubes on the external wall of reactor, and using cooling medium.

The raw materials, solvents and catalysts (including the solvent and catalyst recycled) which are mixed together come into the top of liquid phase of reactor, and use the circle air distributor to blow into compressed air or other oxygen-containing gas (or blow into oxygen-containing gas from the drilled holes on the reactor wall) from the bottom and middle place. Inside the reactor, the materials travels from top to bottom, and come out from the bottom of reactor by level control. Basically, the material flow is a plunger-flow.

The control principle of reaction is also that: increase the concentration of TA inside oxidation reactor as high as possible without forming crystal by the method of controlling the feeding quantity and discharge quantity of PX, acetic acid and water. TA forms crystal in crystallizer system only.

If TA forms crystal at the low temperature zone on the top of reactor, the crystal will deposit at the high temperature zone (equilibrium zone) and completely dissolve, and also the 4-CBA inside TA crystal will be quickly oxidized into TA.

⑤ Combination of Oxidation Reactors

Figure 3:
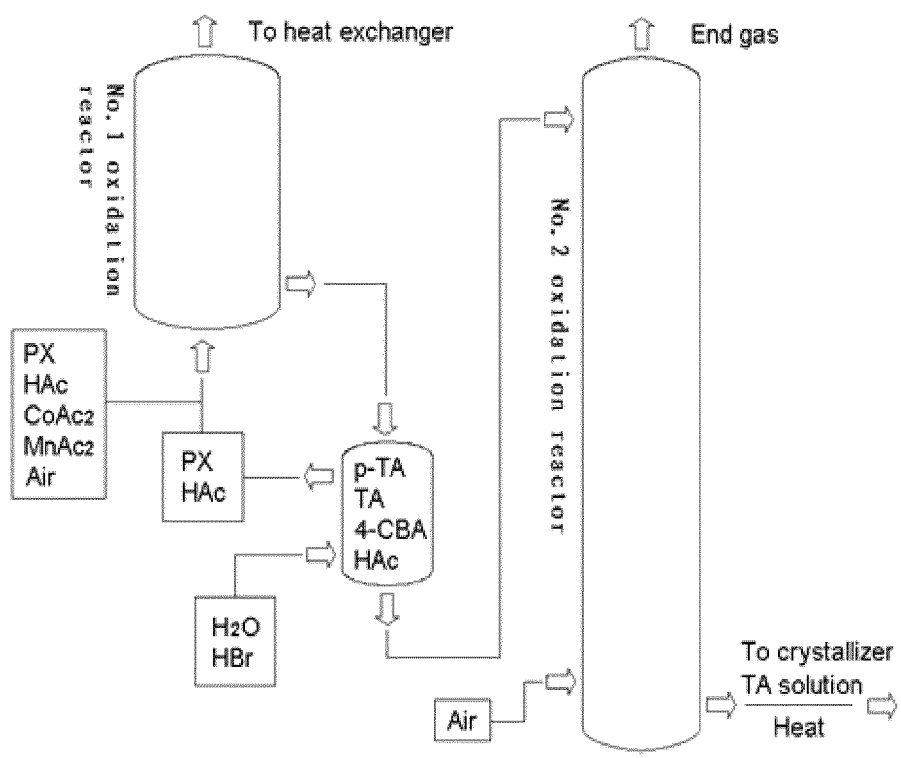
FIG. 3 Schematic diagram of the oxidation reactors in series.

FIG. 3 shows the schematic diagrams of two oxidation reactors in series. The first oxidation reactor uses PX as its raw material, compressed air a its auxiliary materials, acetic acid (HAc) as solvent, cobalt acetate and manganese acetate as catalysts, methyl benzoic acid (p-TA) as its target product, while forming terephthalic acid (TA), p-tolualdehyde (TALD), carboxy benzaldehyde (4-CBA), and the like. Remove PX and partial acetic acid from the material out from the outlet of the first oxidation reactor; add water as its co-solvent; add hydrobromic acid (HBr) as co-catalyst. Then, the resulting product is fed to the second oxidation reactor.

From the bottom of the second oxidation reactor, TA is in a fully dissolved state, p-TA and 4-CBA will be completely oxidized into TA, rather than it will not be present in TA crystals as impurity. TA solution from the bottom of the second oxidation reactor is fed to a crystallizer. The heat generated by the oxidation reaction is removed together with solvent water and acetic acid, where is recovered by both crystallizer and heat exchanger.

Alternative Combination Method (the First Oxidation Reactor):

A. Apply a general oxidation reactor (mixed oxidation) as the first oxidation reactor, Oxidation processes includes: 1) pressure oxidation; 2) atmospheric oxidation.

B. Apply the oxidation reactor with the structure of inner and outer chambers (or the oxidation reactor with the structure of internal, medium and outer chambers) as the first oxidation reactor, as shown in FIG. 2.

Oxidation processes includes: 1) pressure oxidation; 2) atmospheric oxidation.

C. Apply a tower type plunger-flow oxidation reactor (including horizontal plug-flow oxidation reactor) as the first oxidation reactor, Oxidation processes includes: 1) pressure oxidation; 2) atmospheric oxidation.

The major process of the first oxidation reactor is low temperature process, the main aim is to obtain the PT acid, and decrease the consumption of acetic acid. The production of a little of TA crystal is permitted. The hydrobromic acid is not added to the first oxidation reactor, the bromide ion plays an important part as cocatalyst for the oxidation of the second methyl.

Atmospheric oxidation is that the heat from oxidation reaction tail gas is recycled by the method of tail gas going through condensation tower, then obtain the crude acetic acid and water by segregation, after this process, the tail gas is directly blow to air to decrease the rating of compressed air and the rating of pressure resistance of oxidation reactor.

Alternative Combination Method (the Second Oxidation Reactor):

A. Apply tower type oxidation reactor as the second oxidation reactor, as shown in FIG. 2. the heat removing method can be solvent flash vaporization, and also can be firstly the decalescence of low temperature deionized water, then flash vaporization in crystallizer.

Oxidation processes includes:
1) Apply compressed air as auxiliary material (the oxygen in the air is oxidant)
2) Apply oxygen as auxiliary material (the oxygen is oxidant)

B. Apply oxidation reactor with the structure of inner and outer chambers (or the oxidation reactor with the structure of internal, medium and outer chambers) as the second oxidation reactor, the advantage is that the reaction heat can be removed by solvent flash vaporization, and finally the concentration of TA solution is relatively higher, and the load of crystallization equipment can be decreased.

Oxidation processes includes:
1) Apply compressed air as auxiliary material (the oxygen in the air is oxidant)
2) Apply oxygen as auxiliary material (the oxygen is oxidant)

2. Crystallizer System

Set up 3-5 sets of tandem crystallizers in the crystallizer system, the crystallization temperatures are decreased in turn. The heat from solvent after flash vaporization through condenser and the solvent are all recycled. After removing the floating solid impurities, the mother liquor separated from crystal coming from the last crystallizer is sent back to recycle systems for solvent and catalyst. Set up stirrer in the crystallizer, so as to distribute the crystal particles in a uniformity dimension to the design demand.

The discharge from oxidation reaction enters into the first crystallizer by level control.

The heat from oxidation reaction is removed by solvent and water in tail gas after flash vaporization. More reaction heat is removed from reaction by the method of solvent flash vaporization in crystallizer, which is different to current processes. Also, the new solvent for crystallization includes acetic acid which results in the high quality demand for materials made of crystallizer, which is different to current processes too.

The recycled water and acetic acid from crystallizer system are sent back to recycle system for water and acetic acid respectively.

3. Add Water as Solvent

Inside oxidation reactor, add water into liquid phase materials in the oxidation reaction zone from PT acid to TA as a secondary solvent of TA, properly increase the reaction temperature, enhance the TA solubility in mixed solvent consisting of water and acetic acid, so that the TA obtained from reaction can be completely dissolved in solvent. Also, the temperature in the reaction zone from PT acid to 4-CBA can be properly increased, so as to increase the reaction velocity of control step of tandem oxidation reaction.

4. Temperature and Pressure of Oxidation Reaction

The Pressure of this Invention has Two Cases:

1) As a single oxidation reactor, the reaction pressure is about 7.2 to 8.0 MPaG, the reaction temperature is about 150° C. to 210° C. and 210° C. to 350° C. respectively by stage control. The typical temperature of low temperature stage is 160° C., the pressure is the same to that in high temperature stage, and this pressure is significantly higher than the saturated vapor pressure of liquid phase materials in low temperature stage. The typical temperature of high temperature stage is 288° C. and about 7.5 MPaG respectively. The temperature control is achieved by the overall balance of the heat of coming in and out of the reactor from solvent flash vaporization in crystallizer and the reaction heat etc.

As the tower type oxidation reactor whose temperature is controlled by stage, the heat can not be removed by solvent flash vaporization, but only add the cold mixed solvent consisting of deionized water and acetic acid to absorb the heat, then remove the heat by the solvent flash vaporization in crystallizer.

Control the reactor pressure by controlling the gas throughput of compressed air or other oxygen-containing gas and the outlet control valve for non-condensable gas from condensation system of reactor tail gas. The pressure is the corresponding saturated vapor pressure at the high temperature zone in reactor, or is slightly higher than this saturated vapor pressure, but the vaporization of liquid phase solvent inside oxidation reactor is not allowed.

Except the oxidation reactor with the structure of inner and outer chambers (or oxidation reactor with the structure of internal, medium and outer chambers), the heat can be removed by the solvent flash vaporization inside reactor.

2) As a oxidation reactor combination, apply low temperature in oxidation reactor with low temperature, and oxidize the PX into PT acid in the presence of acetic acid solvent (containing a little of water, such as, the water content is 6% or 8%), the reaction temperature is 120° C. to 210° C., typical temperature is 130° C., and pressure is 0.1 to 0.5 MPaG respectively; The temperature for oxidation reactor with high temperature is 210° C. to 350° C., typical temperature is 288° C., and pressure is about 7.5 MPaG. The reaction heat in oxidation reactor with low temperature can be removed by solvent flash vaporization, and the reaction heat in oxidation reactor with high temperature can be removed by solvent flash vaporization in crystallizer.

Example 1:
Taking One Tower Oxidation Reactor for an Example of the Compressed Air as Auxiliary Material:

FIG. 4 is the structural representation of a tower oxidation reactor. The top of the reactor is in the gaseous phase region; the middle and the bottom of the reactor are in the liquid phase region; and the bottom of the reactor is in the equilibrium area. From top to bottom in the middle of the reactor, control their temperatures by adding acetic acids with different water contents, thereby keeping the reactor temperatures at 130° C., 150° C., 180° C., 210° C., 240° C., 260° C., 280° C., 288° C., respectively; in various solvents, the water contents in acetic acid are 6%, 20%, 30%, 40%, 50%, 60%, 70%, 80%, respectively; various solvents are added to different positions at the different temperatures of 130° C., 130° C., 180° C., 210° C., 210° C., 240° C., 240° C., 260° C. and 280° C.; the compressed air (or oxygen, or other oxygen-containing gases) is (are) passed through the border between middle and bottom of the reactor and its lower side; from the upper part, control the temperature at 210° C. And add cocatalyst—hydrobromide (HBr) to the reactor. Nitrogen and carbon dioxide are emitted from the top of the reactor; water, acetic acid and the solution of TA are withdrawn from its bottom, the heat from oxidation reaction is removed with the solution (except for that carried by nitrogen); the control of the heat balance and temperature inside reactor is achieved through controlling the additions of solvents at different temperatures and concentrations.

The Following are Examples of the Dimensions of the Reactor:

Apply a tower type oxidation reactor with the diameter of 4500 mm, and with the height of 28000 mm, apply paraxylene (PX) as material, acetic acid as start solvent, cobalt acetate, manganese acetate as catalyst, and hydrobromic acid as cocatalyst, the ion content (the sum of ion mass) of cobalt, manganese and bromine of effective ingredients in catalyst and cocatalyst is 1050 ppm, the proportion of cobalt to manganese to bromine is 1:1:1. The feed-in proportions (as mass) of start materials of PX, acetic acid, and water are respectively 28%, 66%, and 6%. The prepared materials and catalysts are fed from the top of oxidation reactor, and the liquid phase materials go downwards.

Feed the compressed air from the bottom and the middle of ⅘ of liquid phase height from upwards to downwards, apply the circle air distributor, the air distributor on the bottom has three circles with the diameters of 2000 mm, 3200 mm, and 4000 mm respectively. Add a crossed distributor in the cirque of 2000 mm. The air distributor in the middle also has three circles with the diameters of 1800 mm, 3000 mm, and 3800 mm respectively. The content of gas quantity of bottom distributor to the total gas quantity is 30%. This design for gas feeding can make sure that the disturbance from bottom liquid phase is little, and the material flow process from upwards to downwards is relatively stable as much as possible, and the materials on the top and intermediates are unable to settle to the bottom.

The inlet pressure of compressed air is 8.5 MPaG. The pressure inside reactor is 7.3 MPaG.

The temperature of liquid phase in oxidation reactor is controlled in four stages.

1) The temperature of liquid phase materials from top to the downwards place in ⅕ is controlled at 130-180° C., preferably 160° C. Apply the tube heat exchanger to remove heat, feed the deionized water with low temperature inside tubes, the water flow direction is from upwards to downwards, the water inside tubes is respectively sent to the various areas with high temperature inside reactor. Apply tubes to heat exchange and heat removed to keep the temperature of the first temperature control area in 160° C.

2) The temperature of liquid phase materials from the place in ⅕ to the downwards place in ⅖ is controlled at 160-246° C., preferably 200° C. Also apply the method of heat exchanger with the cold water tubes to remove heat at this area, at the same time, take out a little of water from tubes, on the one hand, limit the temperature, on the other hand, control the total water content in liquid phase materials to be less than 20% by calculating the feeding quantity of PX and acetic acid, and calculating the inflow quantity of deionized cold water.

If control the quantity of compressed air, the place where liquid phase oxidation reaction is completed can move downwards, so the temperatures at the two areas mentioned above is unable to be out of control, and increased uncontrolled.

Because the conditions are not rigor at the two areas, a little of oxygen can be snatched by organic materials to carry out the oxidation reaction, so the oxygen content of oxidized tail gas on the top of reactor is less than 1.5% to 2%. Compared to the current mixed oxidation technology for PX, the utilization rate of compressed air is increased by 10%.

3) The temperature of liquid phase materials from the place in ⅖ to the downwards place in ⅘ is controlled at 210-300° C., preferably 288° C. At this area, balance the increasing trend of temperature of liquid phase materials resulted from exothermic oxidation reaction by adding deionized water with high temperature of 100-250° C. to stabilize the liquid temperature. The deionized water with high temperature can be sprayed from the reactor side wall or sprayed using a circle distributor. Apply the nozzle of deionized water or circle distributor by the method of one for use and one for standby alternatively (or one for use and two for standby) to make sure that the TA crystal which is deposited and crystallized near the nozzle or crystallized on the circle distributor is dissolved.

The method that spraying water by circle distributor and from nozzle of reactor side wall can be quit, but apply the uniformity spraying water by tubes at this area to absorb the heat from oxidation reaction to maintain the reaction temperature.

The oxidation reaction from PT acid to TA is completed at this area.

4) The temperature of liquid phase materials from the place in 4/5 to the bottom is controlled at 285-300° C., preferrably 288° C. Actually control it in the range of 288-289° C. Set up four test points from top to bottom at this area, that the temperature of the second test point is 0.1 V higher than the first test point is permitted, and the temperature of the third test point is the same to the temperature of the second test point. When the temperature at this area has the increasing trend, make sure that the completion process of oxidation reaction move upwards by increasing the supply of compressed air bottom and the total supply of compressed air, or decreasing the feed-in velocity of PX material, so as to ensure that the reactant of organic material phase are all oxidized into TA at this area.

The main ingredient of oxidized tail gas is nitrogen, a little of carbon dioxide, carbon monoxide, and trace acetic acid and other organic ingredients. The pressure is 7.3 MPaG, a great deal of inertia tail gas can be used in power recycle.

The process is different from the current PX oxidation process, in which there is no heat withdraw by a great deal of solvent flash vaporization on the top of reactor, the temperatures of liquid phase from top to bottom at the reactor forms gradient, except that part of the heat are taken out by inert gases on the top of reactor, most of the reaction heat are removed by heating deionized water and the exothermic flash vaporization of deionized water in crystallizer.

The outlet from oxidation reactor bottom is TA solution, wherein the TA is 17.3%, acetic acid is 24.1%, and water is 57.6%. The TA solution is sent into the first crystallizer and flash vaporized and crystallized at 255° C., about 10% of TA is crystallized into crystal. Set up distillation tower on the top of crystallizer to recycle the residual heat, and separate the acetic acid and water preliminarily. Refine the acetic acid, then use it as solvent of preparing PX material, add the water which is used as deionized cooling water for the third temperature control area into reactor to control temperature.

The residual solution from the first crystallizer is sent into the second crystallizer, and flash vaporized and crystallized at 200° C., about 7% of TA is crystallized into crystal. Set up distillation tower on the top of crystallizer to recycle the residual heat, and separate the acetic acid and water preliminarily.

The residual solution from the second crystallizer is sent into the third crystallizer, and flash vaporized and crystallized at 150° C., about 0.8% of TA is crystallized into crystal. Set up distillation tower on the top of crystallizer to recycle the residual heat, and separate the acetic acid and water preliminarily.

The residual solution from the third crystallizer is filtered to remove the solid impurities, a part of it is sent into recycle system for mother liquor to recycle the catalyst and remove the soluble impurities, the other mother liquor are used as the cooling medium of liquid phase materials inside oxidation reactor—deionized cooling water (the actual temperature is much higher, but compare with the liquid phase materials inside reactor, the temperature is lower).

Acetic acid wash (remove the catalyst and cocatalyst of cobalt, manganese, and bromine, also this process can be omitted), separate, and dry the CTA crystal obtained from crystallizer system, and then water wash, separate, and dry it, obtain the PPTA production wherein the contents of 4-CBA and PT acid are all less than 15 ppm.

PPTA yield per hour is 120 t. The consumption of PX per PPTA product is 652 kg/t, the consumption of fuel and power is 100 kg standard oil per ton. the consumption of acetic acid is 20 kg/t.

Example 2:

Take One Twoe Oxidation Reactor Applying Oxygen as Auxiliary Material for Instance:

As shown in FIG. 4, its difference is in the use of oxygen instead of air, through which is passed from the original entrance position of air. The items out of the top are small amounts of only carbon dioxide and carbon monoxide and water and acetic acid as well.

The reactor structure and reaction processes are similar to example 1, except that the auxiliary materials are oxygen instead of compressed air.

In order to avoid using a large flow rate of air compressor with high pressure, this device applies the liquid oxygen supplied by air separation unit as oxidant material. The liquid oxygen is sent into evaporator by a high-pressure pump (or high-velocity pump), the cooling energy is recycled in the evaporator, and the gasified oxygen is fed into oxidation reactor from bottom. Because the total quantity of oxygen gas is relatively less than compressed air, the disturbance to liquid phase at bottom resulted from gas travelling upwards can be very little, make sure that the flow of liquid phase materials is relatively more stable as much as possible, and it is more closed to plunger-flow, the materials on the top and the intermediate products are unable to deposit to the bottom quickly.

Also because the water content in liquid phase materials at the place of feeding oxygen is up to 59%, the sum of organic phase is about 41%, the condition of violent oxidation reaction does not occur. Along with the oxygen-containing gas travelling upwards, the water content in liquid phase decreases, and the oxygen concentration in oxygen-containing gas reduces step by step. Control the oxygen content in tail gas from reactor to be less than 1-2%, so as to ensure the safety of oxidation reactor and increase the utilization rate of oxygen.

As a substitute, instead of adding cooling water into reactor by the circle distributor and by the water nozzle on the side wall of reactor, set up the tube heat exchanger where the water flows from top to bottom inside reactor, add the deionized cooling water at the temperature of 36 into tubes, the water outlets inside tubes are dispersed at different heights of liquid phase at reactor, the water quantity is large where the reaction heat is large, so as to keep the temperatures at different areas stable. The advantages of this project are: 1. Get the heat from the liquid phase materials from upside to downside in turn to keep the increasing temperature gradient from up to downward towards liquid phase materials; 2. Decrease the temperature differences between water outlet of tubes and the liquid phase materials at the places of water outlets to avoid the TA depositing on exchanger wall. The quantity of deionized water entering into tubes is 133 t/h.

Wherein there is no water discharged at the first temperature control area, it absolutely depends on the tube exchanger to get heat; there is 48 t/h of water discharged in uniformity from top to bottom at the second temperature control area, it depends on the tube exchanger to get heat and absorb reaction heat by neutralizing and diluting the liquid phase materials with low temperature water; there is 85 t/h of water discharged in uniformity at the third temperature control area, it depends on the exchanger to get heat and absorb reaction heat by diluting the liquid phase materials with a relative low temperature water (actual temperature is 200-280° C.) to keep the liquid phase temperature at 288° C. The water outlet locations and the water quantities at the outlet locations depend on the amount of holes on the different outlet locations of tubes.

The outlet from oxidation reactor bottom is TA solution, wherein the TA is 17.5%, acetic acid is 23.5%, and water is 58.2%. The TA solution is sent into the first crystallizer and flash vaporized and crystallized at 255° C., about 10% of TA is crystallized into crystal. Set up distillation tower on the top of crystallizer to recycle the residual heat, and separate the acetic acid and water preliminarily. Refine the acetic acid, then use it as solvent of preparing PX material, add the water which is used as deionized cooling water for the third temperature control area into reactor to control temperature or send it to the water tanks.

Example 3:

for the combination with two oxidation reactors instance: wherein the first oxidation reactor apply tower type reactor with the auxiliary material of compressed air; Apply a tower type reactor with the auxiliary material of oxygen at the second oxidation reactor.

Apply a tower type oxidation reactor with the diameter of 4000 mm, and with the height of 24000 mm as the first oxidation reactor, apply paraxylene (PX) as material, acetic acid as start solvent, cobalt acetate, manganese acetate as catalyst, the ion content (the sum of ion mass) of cobalt and manganese of effective ingredients in catalyst is 700 ppm, the proportion of cobalt to manganese is 1:1. The feed-in proportions (as mass) of start materials of PX, acetic acid, and water are respectively 30%, 64%, and 6%. The prepared materials and catalysts are fed from the top of oxidation reactor, and the liquid phase materials go downwards. The feed-in flow rate of PX is 128 t/h.

Blow into compressed air from the bottom of reactor, the reaction heat is removed from the top of reactor by solvent flash vaporization, then recycle the heat by heat exchanger which can be a condensation tower, after removing a little of acetic acid, part of the water is sent back to the oxidation reactor. The water content inside reactor is 8-20%, the typical water content is 12%. Control the oxygen content in tail gas from reactor to be less than 1-3%, so as to ensure the safety of oxidation reactor and increase the utilization rate of compressed air.

The inlet pressure of compressed air is 0.5 MPaG. The pressure inside reactor is 0.1-0.3 MPaG. The reaction temperature is 120-160° C., the typical temperature is 128-130° C. Because it is difficult to oxidize PT acid further, and without the cocatalyst of hydrobromic acid inside system, in this condition, the PX is mainly oxidized into PT acid, and a little of PT acid can be further oxidized into TA and deposit in the form of crystal.

There is no PX near the outlet area at the bottom of reactor. The materials come out from bottom, and are vaporized and concentrated to remove the acetic acid, water, and a little of PX to obtain the mixture consisting of 73% PT acid, 15% TA, 8% acetic acid, and 4% water. In the proportion of 1:2.5, mix and beat this mixture with deionized water into slurry, add the hydrobromic acid as cocatalyst according to the PX content of 350 ppm (ion mass concentration), and the cobalt and manganese catalysts added in the first stage still exist and are available. Send the slurry into the upside of liquid phase at the reactor with a high velocity pump.

The second oxidation reactor applies a set of tower type oxidation reactor (or oxidation reactor with the structure of inner and outer chambers, or oxidation reactor with the structure of internal, medium, and outer chambers, or horizontal plug-flow oxidation reactor) with the diameter of 4500 mm, and the height of 28000 mm. Apply oxygen (or compressed air) as auxiliary material.

The liquid phase temperature at the second oxidation reactor is 285-300° C., the typical temperature is 288° C. Temperature is the first control factor, pressure is the second. Apply solvent flash vaporization to remove heat that the vapor comes out of the reactor from the top of reactor, the solvent consisting of water and acetic acid is segregated by condensation tower on the top of oxidation reactor, then the water and acetic acid are respectively enter tanks. Heat up the vapor by segregation tower to recycle the heat. Part of condensation water is sent back into oxidation reactor to make sure that the proportion of acetic acid and water of solvent phase inside reactor is 1:4 to 1:99, and the typical proportion is 3:17.

Because the water content in liquid phase materials at the place of feeding oxygen is up to 61%, the sum of organic phase is about 39%, the condition of violent oxidation reaction does not occur. Control the oxygen content in tail gas from reactor to be less than 1-2%, so as to ensure the safety of oxidation reactor and increase the utilization rate of oxygen.

Because of the exothermic reaction of liquid phase materials at the bottom of reactor, result in the local warming (or trend), and the water and acetic acid is gasified and ascended, then the water and acetic acid vapors arrive into the gas phase at the top of reactor, enter segregation tower, so that the heat is removed. The ascending process of vapors has a disturbance effect on the plunger-flow travelling downwards of liquid phase materials, but it is unable to result in the top material containing PT acid quickly depositing into bottom. The TA crystal in the slurry added from the top of liquid phase at the reactor dissolves very quickly during the deposition process, and the 4-CBA contained in TA crystal is also oxidized into TA very quickly.

The inlet pressure of oxygen is 8.1 MPaG. The pressure inside reactor is 7.3-7.5 MPaG.

The main ingredient of oxidized tail gas is a little of oxygen, carbon dioxide, carbon monoxide, and trace acetic acid and other organic ingredients. The pressure is 7.5 MPaG.

The outlet from oxidation reactor bottom is TA solution, wherein the TA is 27%, acetic acid is 11%, and water is 72%. The TA solution is sent into the first crystallizer and flash vaporized and crystallized at 255° C., about 19.5% of TA is crystallized into crystal. Set up distillation tower on the top of crystallizer to recycle the residual heat, and separate the acetic acid and water preliminarily. Refine the acetic acid, then use it as solvent of preparing PX material, add the water which is used as deionized water for the second oxidation reactor into reactor to complement the a secondary solvent water, decrease the concentration of acetic acid and reduce the consumption of acetic acid.

The residual solution from the first crystallizer is sent into the second crystallizer, and flash vaporized and crystallized at 200° C., about 7% of TA is crystallized into crystal. Set up distillation tower on the top of crystallizer to recycle the residual heat, and separate the acetic acid and water preliminarily. Crude acetic acid and water are respectively sent into tanks.

The residual solution from the second crystallizer is sent into the third crystallizer, and flash vaporized and crystallized at 150° C., about 0.8% of TA is crystallized into crystal.

The residual solution from the third crystallizer is filtered to remove the solid impurities, a part of it is sent into recycle system for mother liquor to recycle the catalyst and remove the soluble impurities, the other mother liquor are used for the beating of PT acid.

Acetic acid wash (remove the catalyst and cocatalyst of cobalt, manganese, and bromine, also this process can be omitted), separate, and dry the CTA crystal obtained from crystallizer system, and then water wash, separate, and dry it, obtain the PPTA production wherein the contents of 4-CBA is less than 10 ppm, and the PT acid is less than 5 ppm.

PPTA yield per hour is 200 t. The consumption of PX per PPTA product is 652 kg/t, the consumption of fuel and power is 99 kg standard oil per ton. The consumption of acetic acid is 9 kg/t.

The invention claimed is:

1. A process for producing a purified terephthalic acid (PTA) comprises the following steps:
    a. Dissolve parxylene (PX) in acetic acid and water; add 50-3000 ppm of cobalt acetate, manganese acetate and hydrobromic acid wherein the ratio of cobalt acetate: manganese acetate: hydrobromic acid is 1:1-2.5:1-3 by mass;
    b. Add above mixture into a first oxidation reactor, add oxygen-containing gas from the bottom of the oxidation reactor while maintain the temperature between 90 and 180° C., and the pressure between 0.1 and 1.8 MPaG, and adjust the concentration of acetic acid down to 90% with water;
    c. Move the mixture resulted from step b to a tower to remove the non-oxidized PX and partial acetic acid, then add water to adjust the concentration of acetic acid down to 20%;
    d. Pump the mixture resulted from step c to the top of a second oxidation reactor, and add oxygen-containing gas at the bottom above the equilibrium zone of the oxidation reactor while maintain the temperature between 260 and 350° C., and the pressure between 7.0 and 8.5 MPaG, and adjust the concentration of acetic acid about 20% with water and acetic acid;
    e. Move the mixture resulted from step d to the bottom of the second oxidation reactor, equilibrium zone, maintain the temperature between 260 and 350° C. and the concentration of acetic acid at 20%;
    f. Crystallize the terephthalic acid (TA) from the mixture resulted from step e by flash vaporization in a crystallizer, wherein the first oxidation reactor is an oxidation reactor consisting of an inner chamber and an outer chamber and the second oxidation reactot is a tower-type of oxidation reactor.

2. The process according to claim 1, wherein 4-carboxyl benzaldehyde (4-CBA) and p-methyl benzoic acid (PT acid) have been excluded in said purified terephthalic acid.

3. The process according to claim 1, wherein the process further comprises adjusting concentrations of cobalt acetate, manganese acetate and hydrobromic acid when the water and acetic acid are added in the steps from a to e.

* * * * *